United States Patent [19]

Ichijima et al.

[11] 4,407,936
[45] Oct. 4, 1983

[54] PROCESS AND MATERIAL FOR FORMING COLOR PHOTOGRAPHIC IMAGE

[75] Inventors: Seiji Ichijima; Toshiyuki Watanabe; Nobuo Furutachi; Nobuo Seto, all of Kanagawa, Japan

[73] Assignee: Fuji Photo Film Co., Ltd., Kanagawa, Japan

[21] Appl. No.: 243,159

[22] Filed: Mar. 12, 1981

[30] Foreign Application Priority Data

Mar. 12, 1980 [JP] Japan .................................. 55-31320

[51] Int. Cl.$^3$ .............................................. G03C 1/40
[52] U.S. Cl. ................................... 430/505; 430/555; 430/387
[58] Field of Search ........................ 430/555, 505, 387

[56] References Cited

U.S. PATENT DOCUMENTS 3,615,506 10/1971 Abbott et al. ....................... 430/555
4,264,723 4/1981 Ichijima et al. ..................... 430/555
4,310,623 1/1982 Watanabe et al. ................... 430/555

*Primary Examiner*—J. Travis Brown
*Attorney, Agent, or Firm*—Sughrue, Mion, Zinn, Macpeak and Seas

[57] ABSTRACT

A color photographic light-sensitive material is described, said material comprising a support having coated thereon at least one silver halide emulsion layer containing a 5-pyrazolone magenta coupler represented by formula (I)

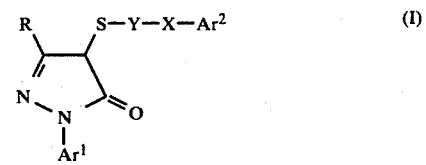

wherein R represents an acylamino group, an anilino group or a ureido group; $Ar^1$ represents a phenyl group which may be substituted with one or more halogen groups, alkyl groups, or alkoxy groups; $Ar^2$ represents a phenyl group or a naphthyl group, each of which may be substituted with one or more halogen groups, hydroxy groups, carboxy groups, cyano groups, alkyl groups, acylamino groups, carbamoyl groups, ureido groups, sulfonamido groups, diacylamino groups, sulfamoyl groups, alkoxycarbonyl groups, phenyl groups, arysulfonyl groups or alkoxy groups; X represents oxygen, sulfur, or a methylene group; and Y represents a straight chain or branched chain alkylene group having from 1 to 6 carbon atoms, or an alkylene group containing an ether bond.

8 Claims, No Drawings

PROCESS AND MATERIAL FOR FORMING COLOR PHOTOGRAPHIC IMAGE

BACKGROUND OF THE INVENTION

This invention relates to a color image forming process and a silver halide photographic light-sensitive material utilizing a novel 2-equivalent magenta color forming coupler (also referred to herein simply as the "magenta coupler").

It is known that, upon color development of a silver halide color photographic material, an oxidized aromatic primary amine color developing agent reacts with a coupler to form an indophenol, indoaniline, indamine, azomethine, phenoxazine, phenazine or like dye, thereby forming color images. Silver halide emulsions selectively sensitive to blue, green and red light, respectively, and yellow, magenta and cyan color image-forming compounds which are in a complementary color relation to the sensitivity of the respective emulsions are employed. For example, acylacetanilide or dibenzoylmethane couplers are generally used for the formation of a yellow color image, pyrazolone, pyrazolobenzimidazole, cyanoacetophenone and indazolone couplers are generally used for the formation of magenta color images, and phenolic couplers (e.g., phenols and naphthols) are generally used for the formation of cyan color images.

In one of the most preferred embodiments of color photographic light-sensitive materials, dye image-forming couplers are added to silver halide emulsions. Couplers added to emulsions must be rendered non-diffusible (or at least diffusion-resistant).

Most conventional color-image-forming couplers are 4-equivalent couplers. That is, the development of 4 mols of silver halide as an oxidizing agent is theoretically necessary to form 1 mol of dye through the coupling reaction. On the other hand, 2-equivalent couplers are also known having an active methylene group substituted with a group (often referred to as "coupling-off group") eliminatable upon oxidative coupling of the coupler with an oxidation product of an aromatic primary amine developing agent. Such 2-equivalent couplers require the development of only 2 mols of silver halide to form 1 mol of dye. Since 2-equivalent couplers require only one-half the silver halide as compared with conventional 4-equivalent couplers to form a dye, their use enables rapid processing of light-sensitive materials due to the thinness of the light-sensitive layers, improvement of the photographic properties due to a reduction in film thickness, and results in economic advantages.

Several approaches have thus far been suggested to produce 2-equivalent 5-pyrazolone couplers (primarily for use as magenta-forming couplers). For example, the substitution of the 4-position of a pyrazolone with a thiocyano group is described in U.S. Pat. Nos. 3,214,437 and 3,253,924, with an acyloxy group is described in U.S. Pat. No. 3,311,476, with an aryloxy group is described in U.S. Pat. No. 3,419,391, with a 2-triazolyl group is described in U.S. Pat. No. 3,617,291, with an oxalic acid ester group is described in U.S. Pat. No. 3,926,631, with a sulfonamido group is described in West German Patent Application (OLS) No. 2,526,112, and with a halogen atom is described in U.S. Pat. No. 3,522,052.

However, in using these 4-position substituted pyrazolone couplers, there are disadvantages, e.g.: serious color fog may result; the reactivity of the couplers may be unsuitable; the couplers may be chemically so unstable that they are converted to materials incapable of color formation over a period of time; and the synthesis of such couplers is often difficult.

Also, it has hitherto been known to substitute the 4-position of a 5-pyrazolone with an alkylthio group, an arylthio group or a heterocyclic ring thio group, as described in U.S. Pat. No. 3,227,554. However, with many of these known thio-substituted pyrazolone compounds, the reactivity with the oxidation product of an aromatic primary amino color developing agent is unsuitable and, further, they are difficult to employ in ordinary color light-sensitive materials due to the strong photographic action of the mercapto compound produced as a result of the coupling reaction. In addition, the chemical stability of these couplers is not generally satisfactory, and the couplers change in quality resulting to a decrease in the color forming density over a period of time after coating, which is usually a fatal defect.

SUMMARY OF THE INVENTION

Therefore, an object of this invention is to provide a novel 2-equivalent magenta coupler in which the coupling position (i.e., the 4-position) is substituted with a group eliminatable upon coupling with an oxidation product of an aromatic primary amine developing agent.

Another object of this invention is to provide a color photographic light-sensitive material having an excellent color forming property which does not change and is stable even when the color photographic material is stored for a long period of time, by means of using a stable coupler.

A further object of this invention is to provide a color photographic light-sensitive material having high sensitivity using a novel 2-equivalent magenta coupler.

A still further object of this invention is to provide a novel 2-equivalent magenta coupler having suitable reactivity and capable of forming a dye in high yield without forming undesired fog or stain.

An additional object of this invention is to provide a novel 2-equivalent magenta coupler which can be easily synthesized and in high yield.

These and other objects of this invention will become apparent from the following detailed description and examples.

Recently, new techniques have been found for synthesizing 5-pyrazolone compounds having various kinds of substituted alkylthio groups as an eliminatable (coupling off) group, and using such techniques new improved couplers which have few of the disadvantages described above have now been found.

Therefore, the objects of this invention can be attained by a process using a novel photographic coupler represented by the formula (I) described below and, particularly by using a color photographic light-sensitive material comprising a support having thereon at least one silver halide emulsion layer and with at least one of the silver halide emulsion layers containing a novel 2-equivalent magenta coupler represented by the formula (I) described below.

The couplers according to this invention are represented by the formula (I)

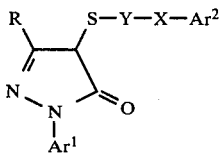

(I)

wherein R represents an acylamino group, an anilino group or a ureido group; $Ar^1$ represents a phenyl group which may be substituted with one or more halogen groups, alkyl groups, or alkoxy groups; $Ar^2$ represents a phenyl group or a naphthyl group, each of which may be substituted with one or more halogen groups, hydroxy groups, carboxy groups, cyano groups, alkyl groups, acylamino groups, carbamoyl groups, ureido groups, sulfonamido groups, diacylamino groups, sulfamoyl groups, alkoxycarbonyl groups, arylsulfonyl groups or alkoxy groups; X represents oxygen, sulfur, or a methylene group; and Y represents a straight chain or branched chain alkylene group having from 1 to 6 carbon atoms which may contain one ether bond (that is, an —O— group).

DETAILED DESCRIPTION OF THE INVENTION

Of the couplers according to this invention, those couplers in which X is an oxygen atom and Y is an alkylene group are particularly preferred in view of the effects according to this invention.

The acylamino groups for R include an aliphatic acylamino group having from 2 to 30 carbon atoms or an aromatic acylamino group having from 6 to 32 carbon atoms, which may be substituted with a halogen group, an acylamino group, an alkoxy group, an aryloxy group, an aryl group, a sulfonamido group, a sulfamoyl group, an alkoxycarbonyl group, an imido group, a cyano group, a carboxy group, an alkylcarbonyl group, an aryloxycarbonyl group, a sulfo group, an acyloxy group, a carbamoyl group, a ureido group, a urethane group, a heterocyclic group, an alkylsulfonyl group, an arylthio group, an alkylthio group, an anilino group, a hydroxy group, an arylsulfonyl group, etc., such as, for example, an acetamido group, a benzamido group, a pentanamido group, a 3-[α-(2,4-di-tert-amylphenoxy)butyramido]-benzamido group, a 2,2-dimethylpropanamido group, a 3-[α-(2,4-di-tert-amylphenoxy)acetamido]benzamido group, a 3-[α-(3-pentadecylphenoxy)butyramido]benzamido group, an α-(2,4-di-tert-amylphenoxy)butyramido group, an α-(3-pentadecylphenoxy)butyramido group, etc.

The anilino groups for R may be substituted with a straight or branched chain alkyl, alkenyl, aralkyl or aryl group, and the same groups as described above for the acylamino group, and have from 6 to 32 total carbon atoms (inclusive of the anilino moiety). Representatove examples include a 2,4,5-trichloroanilino group, a 2-chloro-5-carboxyanilino group, a 2,4-dichloroanilino group, a 2-chloro-5-tetradecanamidoanilino group, a 2-chloro-5-(2-octadecenylsuccinimido)anilino group, a 2-chloro-5-[α-(3-tert-butyl-4-hydroxy)tetradecanamido]anilino group, a 2-chloro-5-(N-succinimido)anilino group, a 2-chloro-5-tetradecyloxycarbonylanilino group, a 2-chloro-5-acetamidoanilino group, a 2-methoxy-5-N,N-diethylsulfamoylanilino group, a 2,4-dichloro-5-tetradecyloxyanilino group, etc.

The ureido groups for R may be substituted by the same groups as above-described acylamino group. Representative examples include a 3-[(2,4-di-tert-amylphenoxy)acetamido]phenylureido group, a phenylureido group, a methylureido group, an octadecylureido group, a 3-tetradecanamidophenylureido group, etc.

$Ar^1$ in the formula (I) can represent a phenyl group which may be substituted with one or more halogen groups (for example, fluorine, chlorine, and/or bromine), straight chain or branched chain alkyl groups having from 1 to 35 carbon atoms, and preferably 1 to 18 carbon atoms, alkoxy groups containing a straight chain or branched chain alkyl group having from 1 to 35 carbon atoms and preferably from 1 to 18 carbon atoms.

$Ar^2$ in formula (I) can represent, in more detail, a phenyl group or a naphthyl group, each of which may be substituted with one or more halogen groups (for example, fluorine, chlorine, and/or bromine), hydroxy groups, carboxy groups, cyano groups, straight chain, branched chain or cyclic alkyl groups having from 1 to 35 carbon atoms, and preferably from 1 to 22 carbon atoms (for example, methyl groups, butyl groups, tert-amyl groups, etc.), acylamino groups having the number of carbon atoms as described above (for example, acetylamino groups, butyramido groups, octadecanamido groups, etc.), carbamoyl groups (for example, N-methylcarbamoyl groups, N,N-diethylcarbamoyl groups, N-methyl-N-dodecylcarbamoyl groups, N-methyl-N-phenylcarbamoyl groups, etc.), ureido groups (for example, N-methylureido groups, N-octylureido groups, phenylureido groups, etc.), sulfonamido groups (for example, octanesulfonamido groups, phenylsulfonamido groups, etc.), diacylamino groups (for example, succinimido groups, phthalimido groups, 2,4-dioxo-3-oxazolidinyl groups, etc.), sulfamoyl groups (for example, N-methylsulfamoyl groups, N-methyl-N-octylsulfamoyl groups, etc.), alkoxycarbonyl groups (for example, methoxycarbonyl groups, tetradecyloxycarbonyl groups, etc.), arylsulfonyl groups (for example, 4-benzyloxyphenylsulfonyl groups, etc.) or alkoxy groups (for example, methoxy groups, dodecyloxy groups, etc.).

Preferred examples of the substituents at the 4-position of the 5-pyrazolone represented by formula (I) are set forth below, but the invention is not limited to these examples.

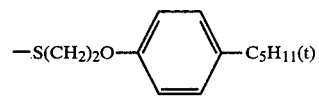

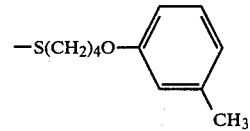

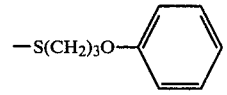

-continued

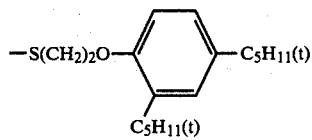
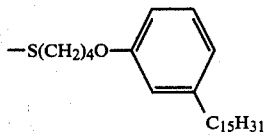
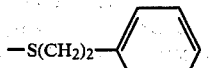
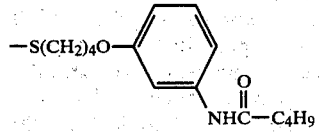
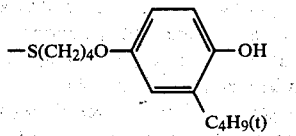
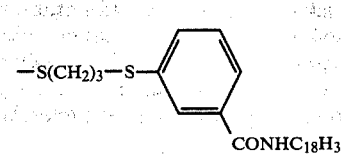
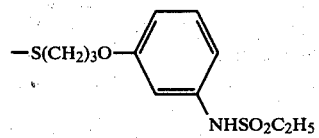
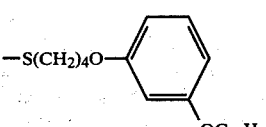
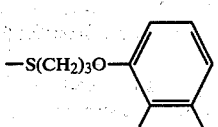
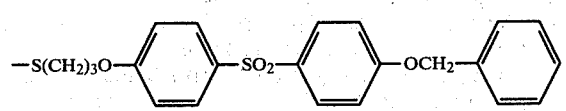

-continued

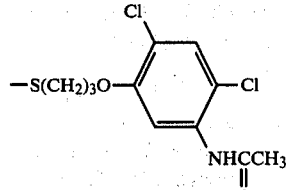
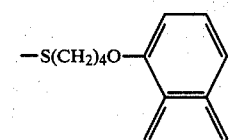
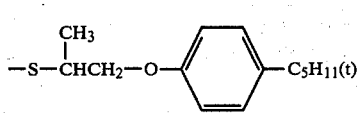
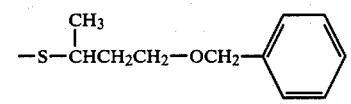
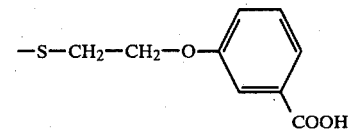
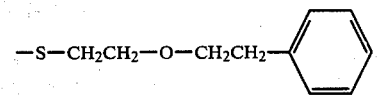
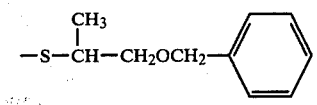
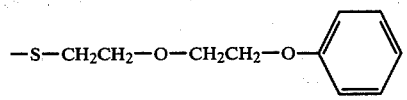

The coupler of this invention represented by formula (I) can be a symmetrical or an asymmetrical complex coupler formed by linking two coupler moieties to each other by the substituents of R and $Ar^1$ or through an R or $Ar^1$ divalent group.

The magenta couplers used according to this invention can provide various properties, depending upon the particular R, $Ar^1$, and $Ar^2$ substituents, and can be employed for various photographic purposes. When at least one of $Ar^1$ and R contains a hydrophobic portion having 8 or more carbon atoms, the coupler is non-diffusible and remains in a hydrophilic colloidal layer of the light-sensitive material. Such a coupler can be incorporated in a silver halide emulsion layer. Couplers having a diffusion-resistant hydrophobic portion in $Ar^2$ and containing a water-solubilizing group such as a sulfo group or a carboxy group in at least one of $Ar^1$ and R provide a diffusible dye through an oxidative coupling reaction with an aromatic primary amine developing agent, although the couplers themselves are non-diffusible. Such couplers which are capable of providing diffusible dyes are particularly useful for diffusion transfer color photography.

The process of forming dye images through the oxidative coupling reaction with an aromatic primary amine developing agent can be classified into two types, depending on the manner of addition of the couplers. One type is a so-called incorporated-coupler process, wherein the couplers are incorporated in an emulsion layer during the production of a light-sensitive material. The other type is a so-called coupler-in-developer process wherein the couplers are dissolved in a developer and are supplied, upon development, through diffusion into an emulsion layer.

Couplers for use in an incorporated-coupler type multilayer system must be immobilized in an emulsion layer, i.e., must be made diffusion-resistant. Otherwise, couplers would migrate through the light-sensitive material and form color in an unintended emulsion layer, having a different color sensitivity, thus seriously degrading the color reproducibility of the light-sensitive material. In order to render the couplers diffusion-resistant, a group having a hydrophobic residue containing from 8 to 32 carbon atoms is introduced into the coupler molecule. Such a residue is called a ballasting group. This ballasting group can be connected to the coupler skeletal structure directly or through an ether bond, a carbonamido bond, a sulfonamido bond, a ureido bond, an ester bond, an imido bond, a carbamoyl bond, a sulfamoyl bond, or the like.

Several specific examples of such ballasting group are described in the specific examples of the couplers of this invention.

Typical examples of the ballasting groups include, e.g., an alkyl group, an alkoxyalkyl group, an alkenyl group, an aryl group substituted by an alkyl group, an aryl group substituted by an alkoxy group, a terphenyl group, and the like. These ballasting groups may be substituted by, for example, a halogen atom (e.g., fluorine, chlorine, etc.), a nitro group, a cyano group, an alkoxycarbonyl group, an amido group, a carbamoyl group, a sulfonamido group, etc. Specific examples of the ballasting group include an n-octyl group, a 2-ethylhexyl group, a tert-octyl group, an n-nonyl group, an n-decyl group, an n-dodecyl group, a 1,1-dimethyldecyl group, a 2,2-dimethyldecyl group, an n-octadecyl group, a 2-(n-hexyl)decyl group, an n-octadecyl group, a 9,10-dichlorooctadecyl group, a heptyloxyethyl group, a 2,4-ditert-amylcyclohexyldodecyloxypropyl group, an oleyl group, a 2,4-di-tert-butylphenyl group, a 2,4-di-tert-amylphenyl group, a 2,4-di-tert-amyl-6-chlorophenyl group, a 3-n-pentadecylphenyl group, a 2-dodecyloxyphenyl group, a 3-heptadecyloxyphenyl group, an o-terphenyl group, a perfluoroheptyl group, etc.

The couplers according to this invention can be synthesized in accordance with the methods described, for example, in Japanese Patent Application (OPI) No. 29805/80 corresponding to U.S. patent application Ser. No. 64,613 filed Aug. 7, 1979. That is, the couplers can be obtained by the reaction of a magenta coupler having a mercapto group in the coupling position with certain halogen compounds in the presence of a base according to the following reaction scheme

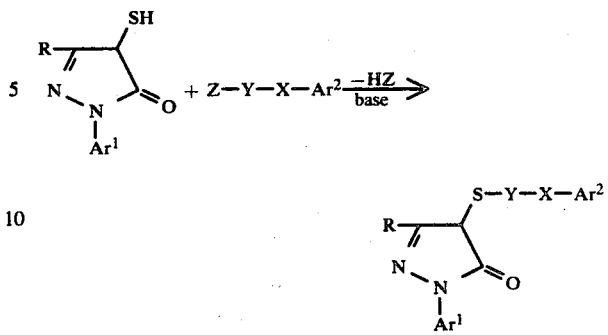

wherein R, X, Y, $Ar^1$ and $Ar^2$ each has the same meaning as defined above, and Z represents a halogen atom (for example, a chlorine atom, a bromine atom, etc.). The 5-mercapto-5-pyrazolones can be synthesized according to, for example, the method in which a thiuronium salt obtained by the reaction of a 4-halogeno-5-pyrazolone with thiourea is hydrolyzed. The reaction between the thus produced 4-mercapto-5-pyrazolone and the halogen compound can be carried out in various kinds of solvents in the presence of a base at a temperature ranging from $-10°$ C. to $100°$ C. Illustrative preferred solvents include alcoholic solvents (e.g., methanol, ethanol, propanol, etc.), aromatic solvents (e.g., benzene, toluene, xylene, etc.), aprotic polar solvents (e.g., acetonitrile, dimethylformamide, hexamethylphosphotriamide, etc.), and the like.

Illustrative preferred bases include an alkali hydroxide (for example, sodium hydroxide, potassium hydroxide, etc.), an alkali metal alkoxide (for example, sodium methoxide, sodium ethoxide, etc.), an organic base (for example, triethylamine, DBU (1,5-diazabicyclo[5.4.0]undecene-5), pyridine, sodium acetate, etc.), and the like. An amount of the base used is preferably 1 to 10 times mol.

Also, it is not necessary that the starting material used for obtaining the compound represented by the formula (I), i.e., a 4-mercapto-5-pyrazolone to be isolated. Thus hydrolysis and thioetherification of the thiuronium compound can be conducted in continuous operation in a reaction vessel, if desired.

The coupler of this invention can advantageously be mixed with a solvent dispersion by dissolving the coupler in a water-immiscible organic solvent having a melting point of about 170° C. or higher, a low-boiling point organic solvent, or a water-soluble organic solvent, or in a high-boiling point, water-immiscible organic solvent and/or a low-boiling point and/or water-soluble organic solvent.

For instance, any of the high-boiling point, water-immiscible organic solvents described in U.S. Pat. No. 2,322,027 can be used as a solvent. Preferred solvents include di-n-butyl phthalate, benzyl phthalate, triphenyl phosphate, tri-o-cresyl phosphate, diphenyl mono-para-tert-butylphenyl phosphate, monophenyl di-o-chlorophenyl phosphate, dioctyl phthalate, dibutyl sebacate, acetyl tributyl citrate, tri-tert-octyl trimellitate, n-nonylphenol, dioctylbutyl phosphate, N,N-diethyllaurylamide, 3-pentadecylphenyl ethyl ether, 2,5-di-sec-amyl-phenyl butyl ether, and so forth.

Low-boiling point organic solvents (having a boiling point of not higher than about 170° C.) or water-soluble organic solvents usable together with or in place of the high-boiling solvents are described in U.S. Pat. Nos. 2,801,171, 2,801,170, 2,949,360, etc. Examples of these organic solvents include the following solvents:

(1) Low-boiling point, substantially water-insoluble organic solvents such as methyl acetate, ethyl acetate, propyl acetate, butyl acetate, isopropyl acetate, ethyl propionate, sec-butyl alcohol, ethyl formate, butyl formate, nitromethane, nitroethane, carbon tetrachloride, chloroform, and so forth.

(2) Water-soluble organic solvents such as methyl isobutyl ketone, β-ethoxyethyl acetate, ethyl acetate, tetrahydrofurfuryl adipate, Carbitol acetate (trademark for diethyleneglycol monoacetate), methoxytriglycol acetate, methyl Cellosolve acetate, acetylacetone, diacetonealcohol, butyl Carbitol, butyl Cellosolve, methyl Carbitol, methyl ethyl ketone, methanol, ethanol, acetonitrile, dimethylformamide, dioxane, and so forth.

Examples of the couplers according to this invention include the following compounds, but the invention is not limited to these couplers.

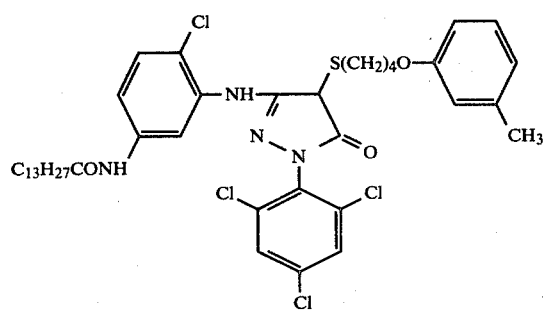

(1)

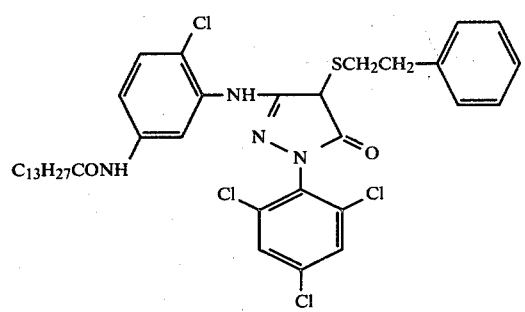

(2)

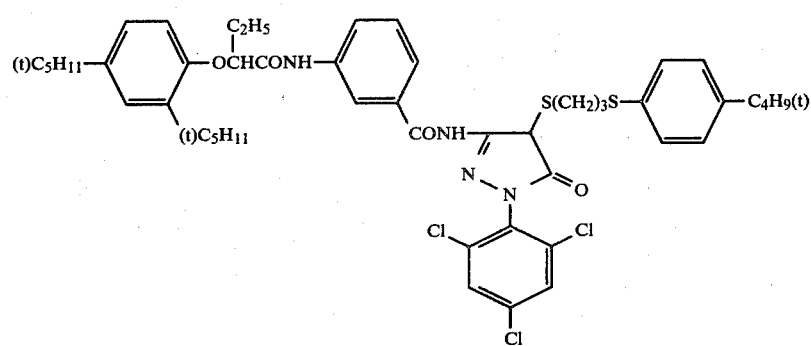

(3)

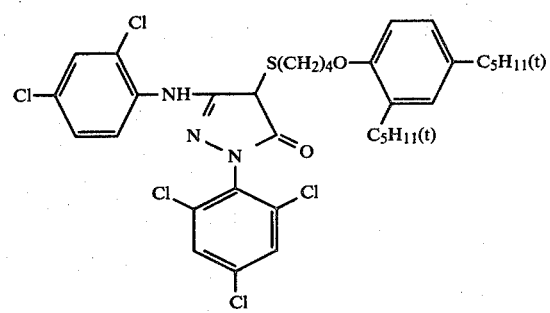

(4)

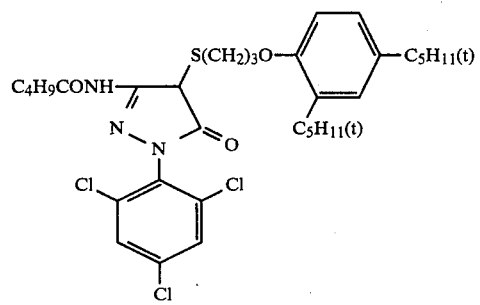
(5)
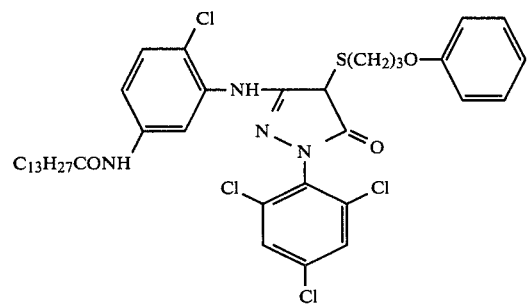
(6)
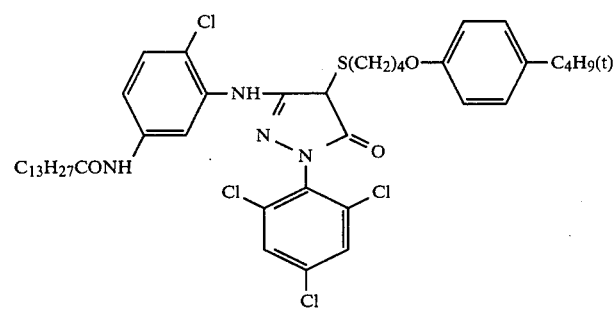
(7)
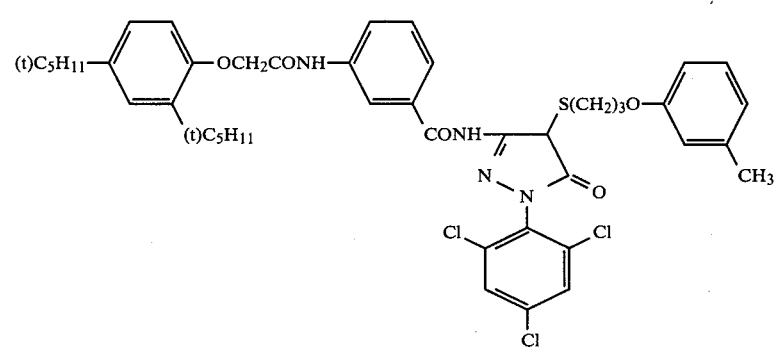
(8)
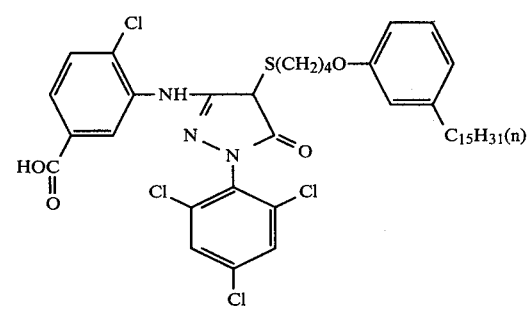
(9)

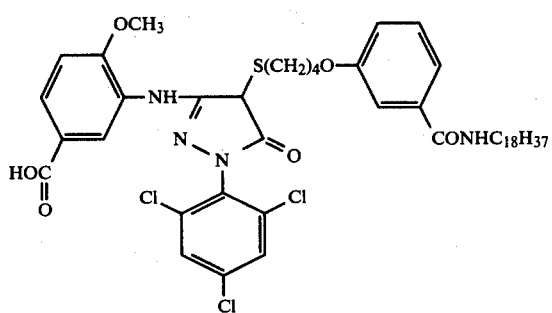
(10)
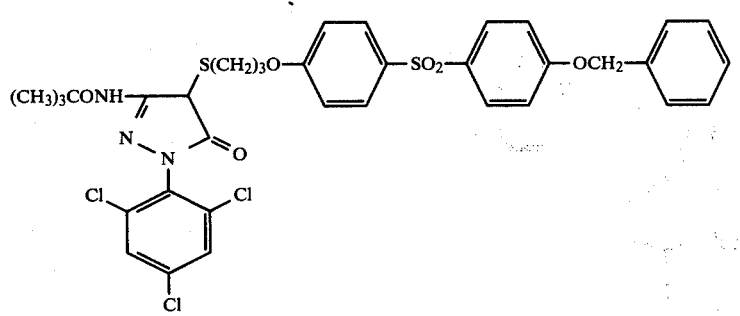
(11)
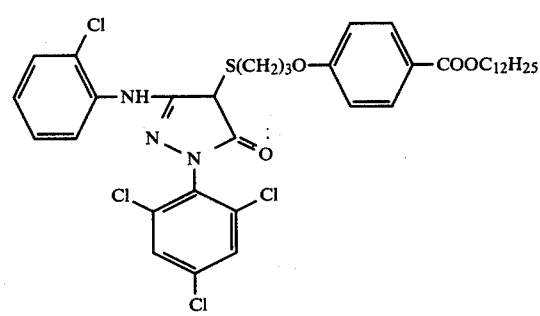
(12)
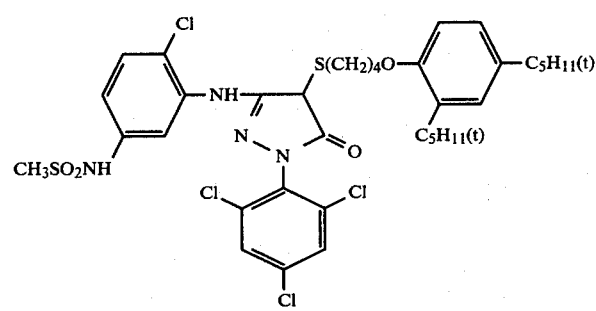
(13)
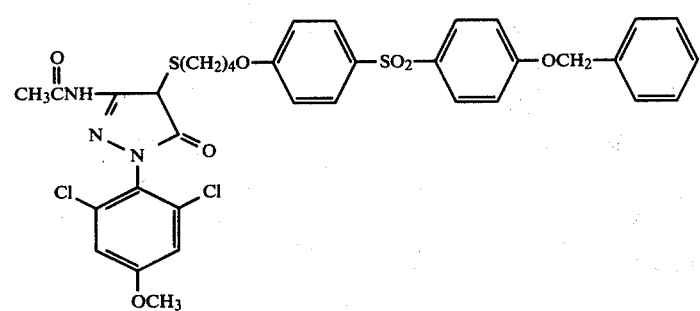
(14)

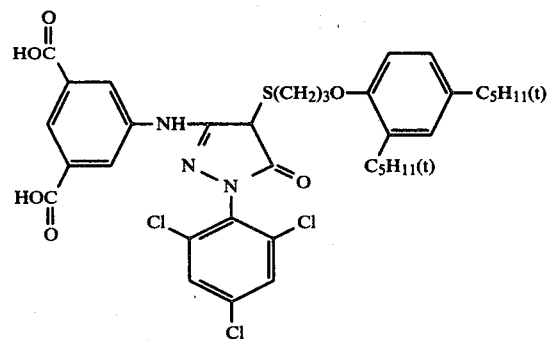
(15)
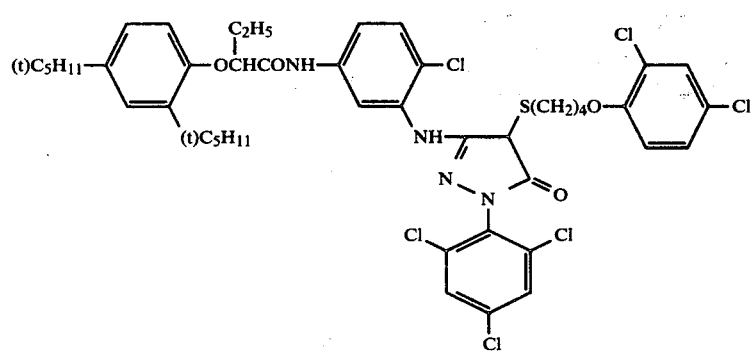
(16)
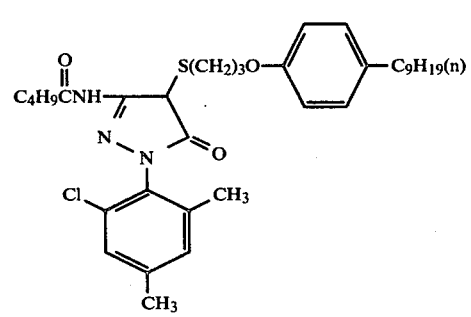
(17)
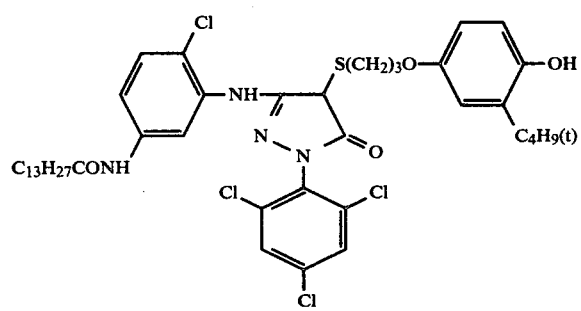
(18)
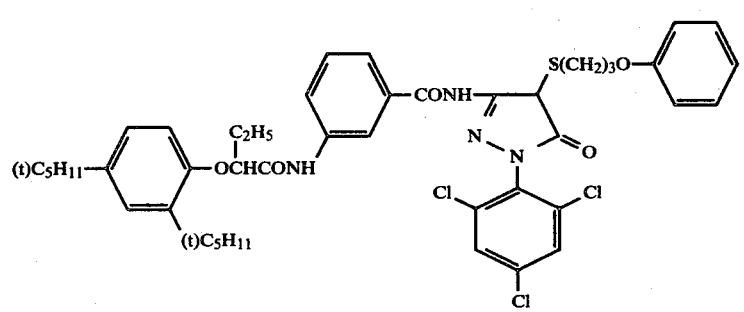
(19)

-continued
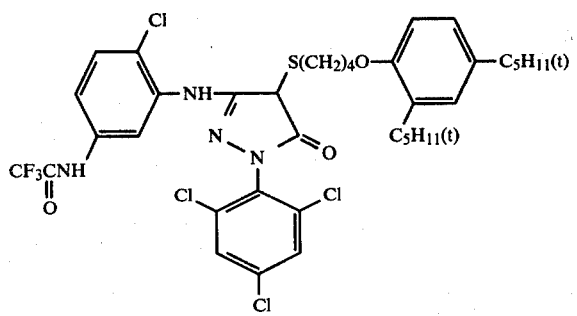 (20)
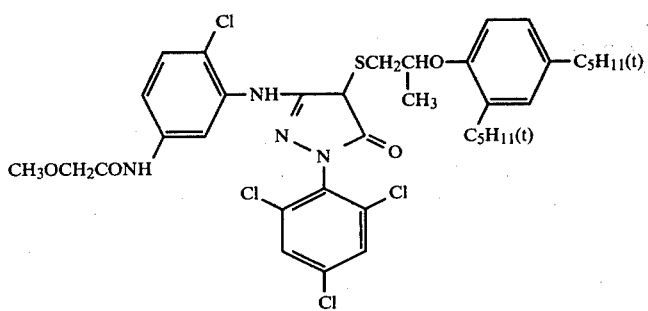 (21)
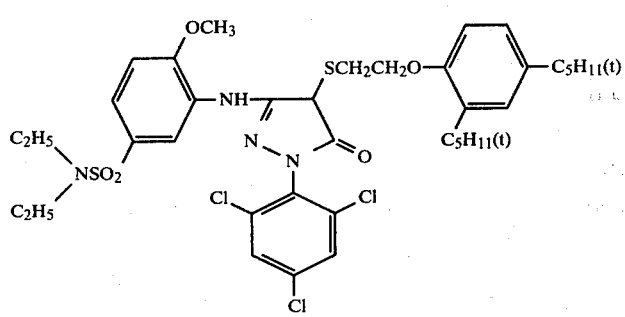 (22)
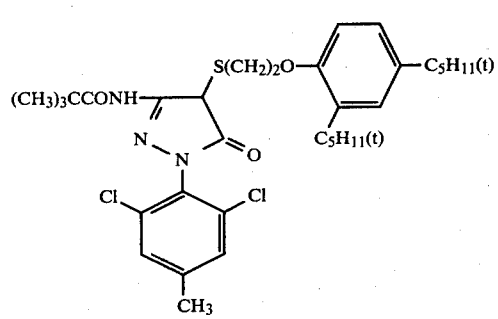 (23)
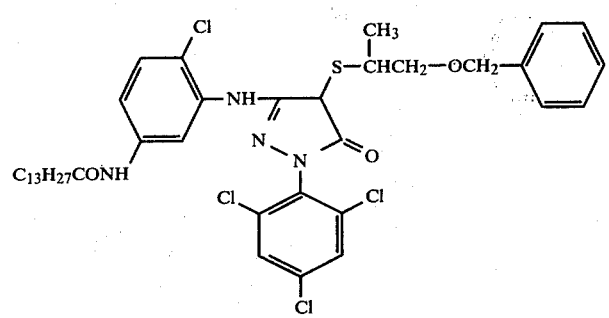 (24)

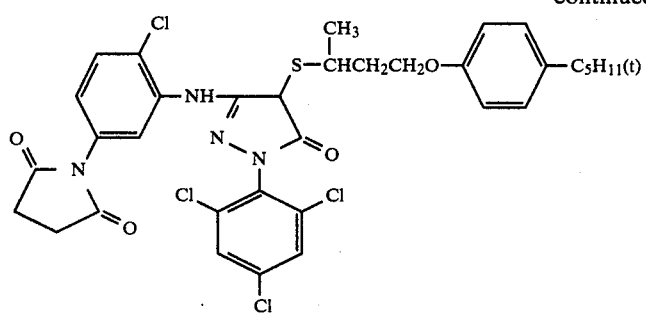
(25)
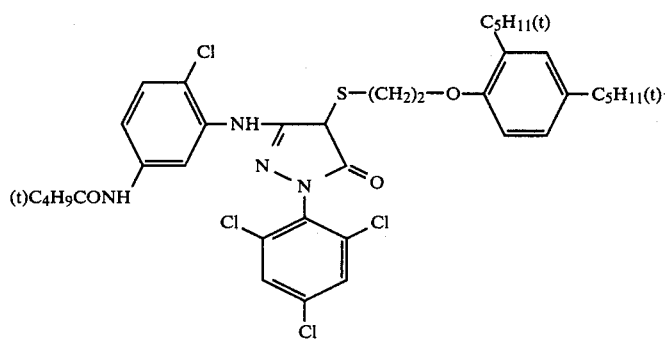
(26)
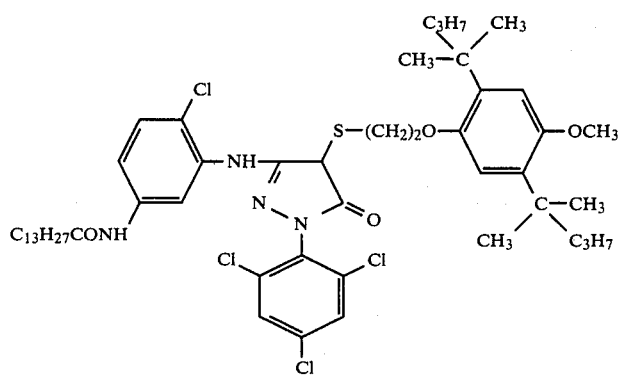
(27)
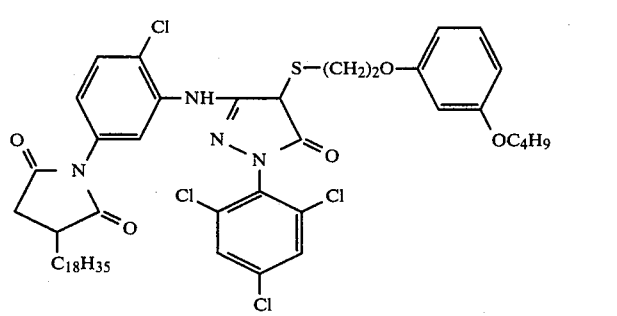
(28)
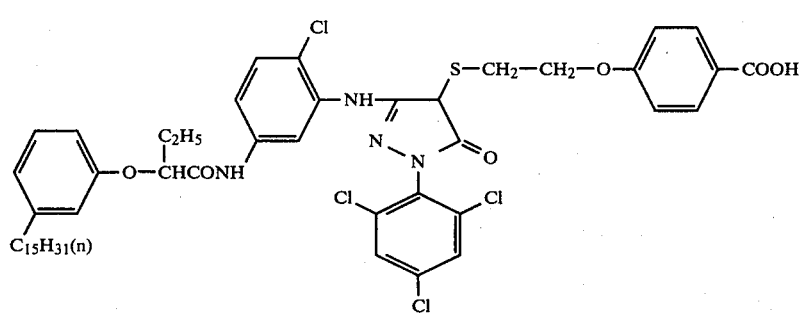
(29)

-continued

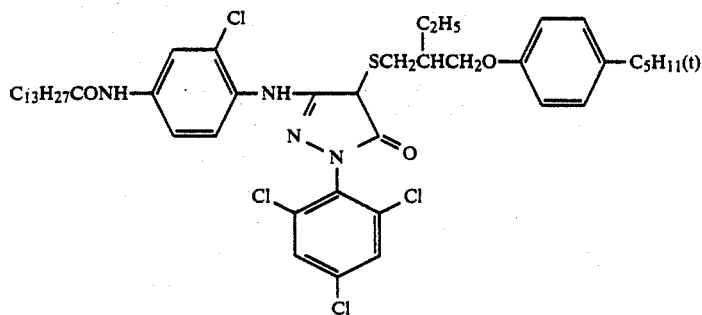

(30)

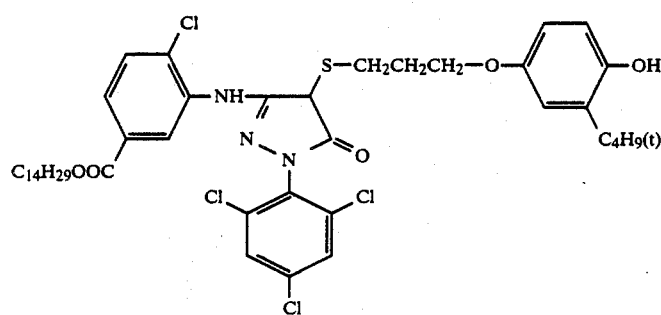

(31)

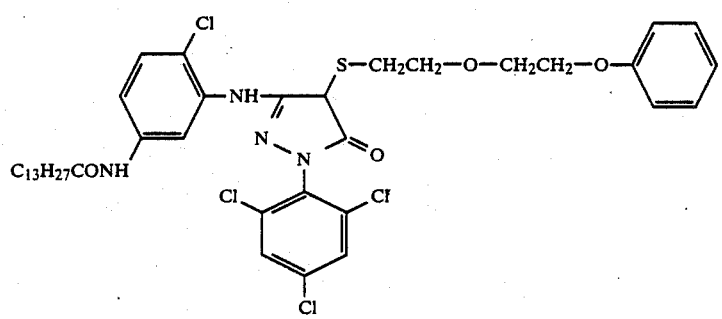

(32)

Representative synthesis examples of the photographic couplers according to this invention are set forth below.

SYNTHESIS EXAMPLE 1

Synthesis of 3-(2-Chloro-5-tetradecanamidoanilino)-1-(2,4,6-trichlorophenyl)-4-[4-(3-methylphenoxy)butylthio]-2-pyrazoline-5-one [Coupler (1)]

Step (1)

Synthesis of S-[3-(2-Chloro-5-tetradecanamidoanilino)-1-(2,4,6-trichlorophenyl)-2-pyrazoline-5-one-4-yl]-isothiuronium hydrobromide 50 g of 3-(2-chloro-5-tetradecanamidoanilino)-1-(2,4,6-trichlorophenyl)-2-pyrazoline-5-one and 6.5 g of thiourea were dissolved in 200 ml of N,N-dimethylformamide. 15.6 g of bromine was added dropwise to the solution and the mixture was stirred at room temperature (25° C.). The reaction mixture was gradually added to 600 ml of water with stirring, and the separated solid was collected by filtration and dried. Thus, 64 g of the desired light gray solid salt was obtained.

Step (2)

Synthesis of 3-(2-Chloro-5-tetradecanamidoanilino)-1-(2,4,6-trichlorophenyl)-4-[4-(3-methylphenoxy)butylthio]-2-pyrazoline-5-one [Coupler (1)]

11.5 g of the isothiuronium salt obtained in Step (1) was added to a solution containing 5 g of potassium hydroxide dissolved in 25 ml of methanol and the mixture was stirred at room temperature. 4.5 g of 4-(3-methylphenoxy)butyl bromide was then added to the solution and the mixture was stirred for 1 hour. After adding 1 liter of ethyl acetate, the mixture was poured into a separating funnel and washed with 1 liter of water. The oil layer was separated, washed with 1 N diluted hydrochloric acid and further washed twice with 1 liter of water. The oil layer was dried with anhydrous sodium sulfate. Ethyl acetate was then removed by distillation under reduced pressure and the residue was recrystallized from acetonitrile to obtain 5.6 g of the desired product. The melting point was 123° to 124° C.

Synthesis Example 2

Synthesis of
3-(2-Chloro-5-tetradecanamidoanilino)-1-(2,4,6-trichlorophenyl)-4-(2-phenylethylthio)-2-pyrazoline-5-one [Coupler (2)]

20 g of the isothiuronium salt obtained in Step (1) of Synthesis Example 1 was added to a solution containing 8.5 g of potassium hydroxide dissolved in 45 ml of methanol. 5.8 g of 2-phenylethyl bromide was then added to the solution and the mixture was stirred at room temperature for 1 hour. After adding 1 liter of ethyl acetate, the mixture was poured into a separating funnel and washed with 1 liter of water. The oil layer was separated, washed with 1 N diluted hydrochloric acid and further washed twice with 1 liter of water. The oil layer was dried with anhydrous sodium sulfate. Ethyl acetate was then removed by distillation under reduced pressure, and the residue was recrystallized from a solvent mixture of acetonitrile and ethyl acetate to obtain 14.8 g of the desired coupler. The melting point was 161° to 162° C.

Synthesis Example 3

Synthesis of
4-[4-(2,4-Di-tert-amylphenoxy)butylthio]-3-(2,4-dichloroanilino)-1-(2,4,6-trichlorophenyl)-2-pyrazoline-5-one [Coupler (4)]

Step (1)

Synthesis of
S-[3-(2,4-Dichloroanilino)-1-(2,4,6-trichlorophenyl)-2-pyrazoline-5-one-4-yl]isothiuronium hydrobromide 42.4 g of 3-(2,4-dichloroanilino)-1-(2,4,6-trichlorophenyl)-2-pyrazoline-5-one and 8 g of thiourea were dissolved in 150 ml of N,N-dimethylformamide. 19.2 g of bromine was added dropwise to the solution and the mixture was stirred at room temperature. The reaction mixture was gradually added to 500 ml of water with stirring, and the separated solid was collected by filtration and dried. Thus, 58 g of the desired light gray solid salt was obtained.

Step (2)

Synthesis of
4-[4-(2,4-Di-tert-amylphenoxy)butylthio]-3-(2,4-dichloroanilino)-1-(2,4,6-trichlorophenyl)-2-pyrazoline-5-one [Coupler (4)]

20 g of isothiuronium salt obtained in Step (1) was added to a solution containing 10 g of potassium hydroxide dissolved in 50 ml of methanol. 12 g of 4-(2,4-di-tert-amylphenoxy)butyl chloride was then added to the solution and the mixture was stirred at room temperature. After adding 1 liter of ethyl acetate, the mixture was poured into a separating funnel and washed with 1 N diluted hydrochloric acid and further washed with water. Ethyl acetate was then removed by distillation under reduced pressure and the residue was recrystallized from a solvent mixture of acetonitrile and ethyl acetate to obtain 28 g of the desired coupler. The melting point was 142° to 144° C.

Synthesis Example 4

Synthesis of
3-{3-[2-(2,4-Di-tert-amylphenoxy)acetamido]benzamido}-1-(2,4,6-trichlorophenyl)-4-[3-(3-methylphenoxy)propylthio]-2-pyrazoline-5-one [Coupler (8)]

Step (1)

Synthesis of
S-{3-[3-(2,4-di-tert-amylphenoxy)acetamido]benzamido-1-(2,4,6-trichlorophenyl)-2-pyrazoline-5-one-4-yl}isothiuronium hydrobromide 50 g of 3-[3-(2,4-di-tert-amylphenoxy)acetamido]benzamido-4-bromo-1-(2,4,6-trichlorophenyl)-2-pyrazoline-5-one and 5.5 g of thiourea were dissolved in 250 ml of methanol. The resulting solution was stirred at room temperature (20° C.) for 1 hour. The reaction mixture was slowly added to 500 ml of water with stirring, and the separated solid was separated by filtration and dried. Thus, 55 g of the desired white solid salt was obtained.

Step (2)

Synthesis of
3-[3-(2,4-di-tert-amylphenoxy)acetamido]benzamido-1-(2,4,6-trichlorophenyl)-4-mercapto-2-pyrazoline-5-one 16 g of potassium hydroxide was dissolved in 400 ml of methanol. After the atmosphere of the reaction container was replaced with nitrogen by introducing nitrogen gas thereto, 55 g of the isothiuronium salt obtained in the Step (1) was added in a powdery state. The mixture was stirred at room temperature for 1 hour. The reaction mixture was added slowly to 800 ml of 1 N diluted hydrochloric acid with stirring, and the separated solid was filtered and dried. Thus, 48 g of the desired light yellow solid compound was obtained. This solid was used for the following step without purifying.

Step (3)

Synthesis of
3-[3-(2,4-di-tert-amylphenoxy)acetamido]benzamido-1-(2,4,6-trichlorophenyl)-4-[3-(3-methylphenoxy)propylthio]-2-pyrazoline-5-one [Coupler (8)]

12 g of potassium hydroxide was dissolved in 400 ml of methanol. 48 g of 3-[3-(2,4-di-tert-amylphenoxy)acetamido]benzamido-1-(2,4,6-trichlorophenyl)-4-mercapto-2-pyrazoline-5-one obtained in the Step (2) was added as a powder and dissolved. 16 g of 3-(3-methylphenoxy)propyl bromide was then added thereto. This solution was stirred at room temperature for 1 hour. After adding 1 l of ethyl acetate, the mixture was poured into a separating funnel and washed with 1 l of water. After the oil layer was separated and washed with 1 N diluted hydrochloric acid, it was washed twice further with 1 l of water. The oil layer was dried with anhydrous sodium sulfate. Ethyl acetate was then removed by distillation under reduced pressure and the residue was recrystallized from a solvent mixture of ethyl acetate and acetonitrile to obtain 39 g of the desired product. The melting point was 129° to 135° C.

The magenta coupler of this invention has such a strong coupling activity for an oxidized aromatic primary amine color developing agent that the oxidation product of the developing agent produced upon color development is rapidly removed, thus accelerating the development of the silver halide emulsion. Suitable amounts of the magenta coupler of this invention are from $2 \times 10^{-3}$ to $5 \times 10^{-1}$ mol, and preferably from $1 \times 10^{-2}$ to $5 \times 10^{-1}$ mol, per mol of silver.

With the magenta coupler of this invention, the process of forming a dye is completed in a color developing bath, which enables the materials to be processed with a beach-fixing bath containing a weak oxidizing agent such as Fe (III) chelate of ethylenediaminetetraacetic acid (EDTA) or the like and a silver complex salt-forming agent or a ferric salt (e.g., ferric chloride) without using a bleaching bath containing a strong oxidizing agent such as potassium ferricyanide or potassium dichromate. This results in a shortening of the time required for the processing steps of color development and minimizes the problem of environmental pollution due to the discharge of processing waste water.

The coupling position substituted magenta couplers of this invention are less inactivated by the action of carbonyl compounds such as aldehydes or ketones, whereas conventionally used coupling position unsubstituted magenta couplers are often changed into compounds having a low color reaction activity such as a methylol or methylenebis compounds when contacted with formaldehyde or the like in the air especially in an emulsion layer, and thus fail to attain sufficient coloration through color development.

The magneta coupler of this invention, when it is used for ordinary color light-sensitive materials, as described in the Examples below, has high stability over a long period of time, and undergoes only a slight reduction in coloring property when stored at a low temperature under high humidity as compared with previously known 2-equivalent couplers. The stability of a color light-sensitive material after production is one of the most important factors in evaluating the characteristics of light-sensitive materials. Also, colored images resulting from the magenta coupler of this invention have markedly superior heat-fastness as compared with couplers which are not substituted in the coupling position. Even in comparison with previously known couplers having the same pyrazolone nucleus and a substitutent at the 4-position, the colored image from the magenta coupler of this invention is found to exhibit greater heat resistance.

The couplers in accordance with this invention can be employed in light-sensitive materials containing a reduced amount of silver halide, i.e., from about several tenths to about 1/100 as much silver halide as the amount in ordinary color light-sensitive materials. For example, suitable amounts of silver for the photographic materials of this invention are $1 \times 10^{-3}$ to $3 \times 10^{-1}$ mol/m². With color light-sensitive materials containing a reduced amount of silver halide, suitable color images can be obtained by, for example, halogenation-bleaching silver deposits formed by color development and again conducting color development to increase the amount of dye produced (for example, U.S. Pat. Nos. 2,623,822, 2,814,565, etc.), or by employing a development processing utilizing color intensification using peroxides or cobalt complex salts to increase the amount of dye produced (for example, West German Patent Application (OLS) No. 2,357,694, U.S. Pat. Nos. 3,674,490, 3,761,265, West German Patent Application (OLS) Nos. 2,044,833, 2,056,359, 2,056,360, 2,226,770, Japanese Patent Application (OPI) Nos. 9728/73 and 9729/73, etc. (The term "OPI" as used herein refers to a "published unexamined Japanese patent application".)).

The 2-equivalent magenta coupler of this invention can be used together with other magenta couplers, as described, for instance, in U.S. Pat. Nos. 2,439,098, 2,369,439, 2,600,788, 2,558,319, 2,311,081, 3,419,391, 3,214,437, 3,006,759, 2,725,292, 3,408,194, 2,908,573, 3,519,429, 3,615,506, 3,432,521, 3,152,896, 3,062,653, 3,582,322, 2,801,171, 3,311,476, British Patent 956,261, Japanese Patent Publication Nos. 2016/69 and 19032/71, Japanese Patent Application (OPI) Nos. 74027/74, 13041/75, 131448/74, 111631/74, 60233/75 and 74028/74; with magentacolored couplers, as described in U.S. Pat. Nos. 2,983,608, 2,455,170, 2,725,292, 3,005,712, 3,519,429, and 2,688,539, British Pat. Nos. 800,262, 1,044,778, 1,464,361 and 1,443,875, Belgian Pat. No. 676,691, West German Patent Application (OLS) No. 2,643,965; with the so-called development inhibitor releasing type couplers capable of imagewise releasing development inhibiting compounds at development, such as, for instance, the monothio type couplers as described in U.S. Pat. Nos. 3,227,550, 3,938,996, 3,227,554 and 4,010,035, British Pat. No. 953,454, the o-aminophenylazo type couplers as described in U.S. Pat. No. 3,148,062, and the couplers as described in Japanese Patent Publication No. 8750/72 and German Patent Application (OLS) Nos. 2,414,006, 2,163,811, and 2,655,871, and also with the hydroquinone releasing development inhibiting compounds as described in U.S. Pat. No. 3,297,445 and British Pat. No. 1,058,606.

One or more of the above-described couplers and the like can be employed in the same layer to achieve the properties required for a particular light-sensitive material and, of course, the same compound can be incorporated in two or more different layers. In general, the couplers are coated at a coverage of from about $1 \times 10^{-4}$ to $5 \times 10^{-3}$ mol/m², and preferably from $3 \times 10^{-4}$ to $2 \times 10^{-3}$ mol/².

In the practice of this invention, known color fading preventing agents as described below can be employed. These fading preventing agents can be used individually or in a combination of two or more thereof. Specific examples of known color fading preventing agents include, for example, hydroquinone derivatives as described in U.S. Pat. Nos. 2,360,290, 2,418,613, 2,675,314, 2,701,197, 2,704,713, 2,728,659, 2,732,300, 2,735,765, 2,710,801 and 2,816,028, British Pat. No. 1,363,921; gallic acid derivatives as described in U.S. Pat. Nos. 3,457,079 and 3,069,262; p-alkoxyphenols as described in U.S. Pat. Nos. 2,735,765 and 3,698,909, Japanese Patent Publication Nos. 20977/74 and 6623/77; p-oxyphenol derivatives as described in U.S. Pat. Nos. 3,432,300, 3,573,050, 3,574,627 and 3,764,337, Japanese Patent Application (OPI) Nos. 35633/77, 147434/77 and 152225/77; and bisphenol derivatives as described in U.S. Pat. No. 3,700,455, etc.

The silver halide emulsion which can be used in this invention can be suitably selected from various kinds of photographic emulsions depending on the end-use purposes of the photographic materials. Suitable silver halides which can be used in this invention include silver chloride, silver chlorobromide, silver bromide, silver iodobromide, and silver chloroiodobromide. Also, suitable binders for the silver halide emulsions which can be used in this invention are gelatin (e.g., alkali process gelatin, acid process gelatin, etc.), gelatin derivatives (e.g., acrylated gelatin as described in U.S. Pat. No. 3,118,766 and graft gelatin having as the branch component a vinyl monomer, such as crylic acid, as described in U.S. Pat. No. 2,831,767), casein, albumin, agar agar, sodium alginate, starch, cellulose derivatives (e.g., carboxymethyl cellulose and hydroxyethyl cellulose), vinyl alcohol, vinylpyrrolidone, polyacrylamide, and the like.

The silver halide emulsions used in this invention can be prepared by a single jet method, a double jet method, a control double jet method, and the halogen conversion method as described in British Pat. No. 635,841 and U.S. Pat. No. 3,622,318.

The silver halide emulsion used in this invention can be sensitized by the natural sensitizers present in gelatin, by a sulfur sensitizer, by a reductive sensitizer, and by a noble metal salt using conventional techniques.

The silver halide emulsion can contain an anti-fogging agent or a stabilizer such as 1-phenyl-5-mercaptotetrazole, 5-methyl-7-hydroxy-1,3,4,7a-tetraazaindene, etc. Also, the silver halide emulsion can contain a sensitizing dye such as a cyanine dye, a merocyanine dye, etc. The silver halide emulsion can contain a coating aid such as saponin, polyethyleneglycol monolauryl ether, etc. Furthermore, the silver halide emulsion can contain a thickener such as polystyrenesulfonic acid, etc., an ultraviolet absorber such as 2-(2-hydroxy-3,5-di-sec-butylphenyl)-5-methoxybenzotriazole, 4-methoxy-α-cyano-cinnamic acid-n-dodecyl ester, etc., an antioxidant or a reducing agent such as sodium bisulfite, ascorbic acid, aminophenols, pyrogallols, gallic acids, catechols, resorcinols, and dihydroxynaphthalenes, and a filter dye such as an oxonol dye and a styryl dye, and other conventional photographic additives, if desired.

A photographic light-sensitive material according to this invention comprises a support having thereon a silver halide emulsion layer containing a 2-equivalent magenta coupler in accordance with this invention. One embodiment of a photographic light-sensitive material according to this invention comprises a multilayered, multicolored photographic light-sensitive material comprising a support having thereon a blue-sensitive silver halide emulsion layer containing a yellow coupler (that is, a coupler that forms a yellow dye), a green-sensitive silver halide emulsion layer containing a magenta coupler (that is, a coupler that forms a magenta dye) in accordance with this invention, and a red-sensitive silver halide emulsion layer containing a cyan coupler (that is, a coupler that forms a cyan dye). Known blue-sensitive silver halide emulsions and the red-sensitive silver halide emulsions can be appropriately used. Open-chain type ketomethylene compounds represented by benzoylacetanilides and pivaloylacetanilides can advantageously be used as yellow color-forming couplers. Phenolic or naphtholic compounds can advantageously be used as cyan color-forming couplers. Such color-forming couplers can contain a coupling off group on the carbon atom of the coupling position, and are desirably non-diffusible.

The photographic light-sensitive material of this invention can have, in addition to the aforesaid silver halide emulsion layers, light-insensitive auxiliary layers such as a protective layer, a filter layer, intermediate layers, an antihalation layer, and a backing layer.

The hydrophilic polymer material, particularly gelatin constituting the layers of the photographic light-sensitive material of this invention can be hardened by various cross-linking agents. For example, although an inorganic compound such as a chromium salt and a zirconium salt, and an aldehyde type cross-linking agent such as mucochloric acid, 2-phenoxy-3-chloromalealdehydic acid, etc., as described in Japanese Patent Publication No. 1872/71 can be used, a non-aldehyde type cross-linking agent; for example, a polyepoxy compound as described in Japanese Patent Publication No. 7133/59, a poly(1-aziridinyl) compound as described in Japanese Patent Publication No. 8790/62, an active halogen compound as described in U.S. Pat. Nos. 3,362,827 and 3,325,287, etc., are particularly useful.

In the photographic light-sensitive materials of this invention, any materials usually used as supports for photographic light-sensitive materials can be suitably used. For instance, preferred examples of such supports are cellulose ester films such as cellulose nitrate films, cellulose acetate films, etc., polyester films such as polyethylene terephthalate films, etc., polyvinyl chloride films, polyvinyl acetal films, polystyrene films, polycarbonate films, polyamide films such as nylon films, baryta-coated papers, α-olefin polymer-coated papers, and so forth.

The photographic light-sensitive material of this invention can be suitably used for various purposes such as color positive films, color negative films, color reversal films, color photographic printing papers, and so forth.

The color photographic light-sensitive material of this invention provides magenta color images having excellent spectral properties and image fastness when imagewise exposed in a conventional manner and processed using conventional color processing steps. The main color processing steps are color development, bleach, and fix; if desired, a wash step can be inserted between some or all the foregoing steps.

A useful color developer which can be used for developing the color photographic material of this invention is an alkaline aqueous solution containing a color developing agent, and having a pH of from about 9.5 to 12.2. Examples of color developing agents which can be used in the color developer include conventional primary aromatic amine color developing agents, such as phenylenediamines (e.g., 4-amino-N,N-diethylaniline, 3-methyl-4-amino-N,N-diethylaniline, 4-amino-N-ethyl-N-β-hydroxyethylaniline, 3-methyl-4-amino-N-ethyl-N-β-hydroxyethylaniline, 4-amino-3-methyl-N-ethyl-N-β-methanesulfonamidoethylaniline, 4-amino-N,N-diethylaniline, 4-amino-3-methoxy-N,N-diethylaniline, 4-amino-3-methyl-N-ethyl-N-β-methoxyethylaniline, 4-amino-3-methoxy-N-ethyl-N-β-methoxyethylaniline, 4-amino-3-β-methanesulfonamidoethyl-N,N-diethylaniline), and p-aminophenols (e.g., 4-amino-phenol, 2,6-dichloro-4-aminophenol, 2-bromo-4-aminophenol, and 2,6-diiodo-4-aminophenol).

The color developer can contain further conventional additives such as, for instance, an alkali metal sulfite, an alkali metal carbonate, an alkali metal bisulfite, a bromide, an iodide, an alkaline buffer, etc. Furthermore, if desired, the color developer can contain a dye forming coupler, a competitive coupler, an antifoggant, a hardening agent, an antioxidant, a thickener, and so forth.

Some of the advantages of this invention are as follows.

(1) Since the amount of silver necessary for obtaining the same magenta color image density can be reduced, the thickness of the light-sensitive layer containing the coupler can be reduced, thus improving the sharpness of the images obtained.

(2) Silver halide color photographic light-sensitive materials having excellent storage stability can be obtained using a coupler according to this invention.

(3) Silver halide color photographic light-sensitive materials having high sensitivity can be obtained using a coupler according to this invention.

(4) Color images with less fog and stain and other excellent photographic properties can be obtained.

(5) The production cost can be reduced through the reduction in the amount of silver halide necessary.

(6) Magenta couplers stable to chemicals such as formaldehyde or acetone can be obtained.

(7) The heat fastness of the magenta color images produced using a coupler according to this invention is improved.

(8) Couplers having a high developing activity can be obtained.

The light-sensitive materials of this invention having the above-described advantages are extremely useful in the field of color photography.

This invention will now be illustrated in more detail by the following non-limiting examples of preferred embodiments of this invention.

EXAMPLE 1

A solution obtained by dissolving 8 g of Coupler (1), and 8.0 ml of dibutyl phthalate, in 25 ml of ethyl acetate while heating at 60° C. was added to 80 ml of an aqueous solution containing 8 g of gelatin, 0.20 g of sodium dodecylbenzenesulfonate at 60° C. The solution mixture was stirred with a homogenizer to prepare a coupler dispersion. The coupler dispersion was mixed with 100 g of a green-sensitive photographic emulsion containing $4.70 \times 10^{-2}$ mol of silver chlorobromide (50 mol% silver chloride) and 9 g of gelatin, and 5 ml of a 3% aqueous solution of 2-hydroxy-4,6-dichloro-s-triazine sodium salt was further added thereto as a hardening agent. After adjusting the pH to 7.0, the dispersion was coated onto a paper sheet having polyethylene coated thereon in a thickness of 3.4 microns (dry thickness; hereafter all thickness given are dry thicknesses). Gelatin was coated thereon (using a 2% gelatin aqueous solution) to form a layer having a thickness of 1 micron to prepare a color print paper (Sample A).

Samples B, C and D were prepared in the same manner as the preparation of Sample A, except that Couplers (2), (4) and (5) according to this invention were employed in place of Coupler (1) described above, respectively, in the equimolar (i.e., 0.01 mol). Also, Samples R, S and T were prepared in a manner similar to the preparation of Sample A, except that Comparison Couplers (L), (M) and (N) having the structures shown below were employed as couplers for comparison in place of Coupler (1), respectively, in the equimolar amount.

Comparison Coupler (L)

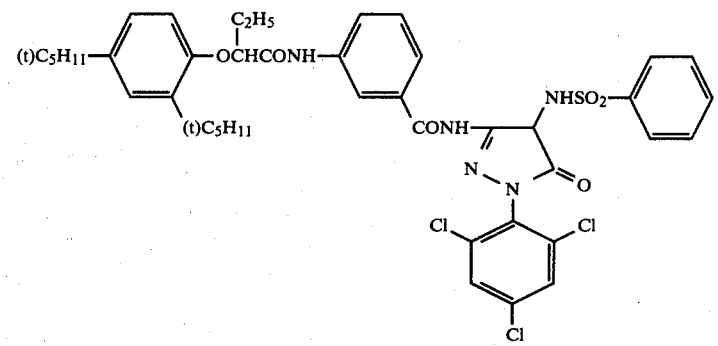

Comparison Coupler (M)

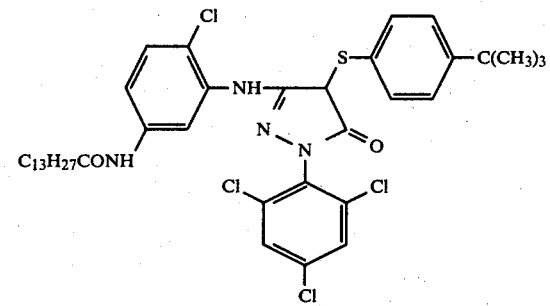

Comparison Coupler (N)

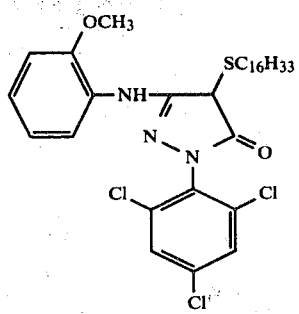

Each of these samples was exposed to green light using a step wedge and processed in the following development processings.

| Processing Step | Temperature (°C.) | Time |
| --- | --- | --- |
| 1. Color development | 33 | 3 min 30 sec |
| 2. Bleach-fixing | 33 | 1 min 30 sec |
| 3. Washing with water | 25 to 30 | 2 min 30 sec |

The processing solutions used had the following compositions:

| Color Development Solution | |
| --- | --- |
| Benzyl Alcohol | 15 ml |
| Diethylene Glycol | 8 ml |
| Ethylenediaminetetraacetic Acid | 5 g |
| Sodium Sulfite | 2 g |
| Anhydrous Potassium Carbonate | 30 g |
| Hydroxylamine Sulfate | 3 g |
| Potassium Bromide | 0.6 g |
| 4-Amino-N—ethyl-N—(β-methanesulfon-amidoethyl)-m-toluidine Sesquisulfate Monohydrate | 5 g |
| Water to make | 1 liter (pH 10.20) |
| Bleach-Fixing Solution | |
| Ethylenediaminetetraacetic Acid | 2 g |
| Ferric Salt of Ethylenediamine-tetraacetate | 40 g |
| Sodium Sulfite | 5 g |
| Ammonium Thiosulfate | 70 g |
| Water to make | 1 liter |

Further, each of these samples coated was also stored under a normal condition, i.e., at 25° C. and 60% relative humidity (RH) for 6 months and then exposed and processed in the same manner as described above. The maximum density of the color image thus obtained was compared with the maximum density of color image obtained by the development processing just after coating. The results obtained are shown in Table 1 below.

TABLE 1

| | | Results of Stability Test | | |
| --- | --- | --- | --- | --- |
| Sample | Coupler | Maximum Density Obtained by Processing just after Coating ($D_1$) | Maximum Density Obtained by Processing after Storage for 6 Months ($D_2$) | $D_2/D_1$ |
| A | (1) | 2.21 | 2.21 | 1.00 |
| B | (2) | 2.20 | 2.18 | 0.991 |
| C | (4) | 2.22 | 2.22 | 1.00 |
| D | (6) | 2.15 | 2.15 | 1.00 |
| R | (L) | 1.95 | 1.23 | 0.631 |
| S | (M) | 1.05 | 0.76 | 0.724 |

TABLE 1-continued

| | | Results of Stability Test | | |
| --- | --- | --- | --- | --- |
| Sample | Coupler | Maximum Density Obtained by Processing just after Coating ($D_1$) | Maximum Density Obtained by Processing after Storage for 6 Months ($D_2$) | $D_2/D_1$ |
| T | (N) | 1.66 | 1.08 | 0.650 |

It is apparent from the results shown in Table 1 that the samples in which magenta couplers according to this invention were used provided extremely good color forming properties, even when the samples were stored under normal condition for 6 months before processing.

EXAMPLE 2

On a transparent cellulose triacetate film support, coating compositions as described below were coated, and then overcoated with gelatin protective layer (1 g/m²), to prepare Samples E to H and U to W.

Coating Compositions

Green-sensitive silver iodobromide emulsion (silver iodide: 6 mol%, silver bromide: 94 mol%)
  Coated amount of silver: 1 g/m²
Magenta coupler described below
  Coated amount: $7 \times 10^{-4}$ mol/m²
Solvent for dispersing coupler: Tricresyl phosphate

| Sample | Coupler |
| --- | --- |
| E | (1) |
| F | (4) |
| G | (5) |
| H | (8) |
| U | (L) |
| V | (M) |
| W | (O) |

Comparison Coupler (O)

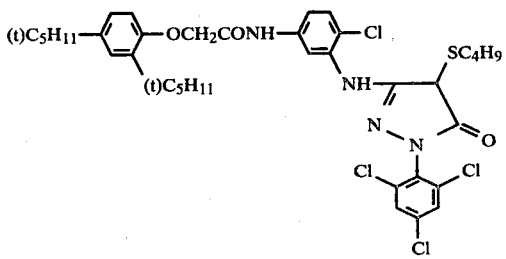

These seven samples were exposed through an optical wedge and then subjected to the following processing steps:

| Processing Step | Temperature (°C.) | Time |
|---|---|---|
| 1. Color development | 38 | 3 min 15 sec |
| 2. Bleaching | " | 6 min 30 sec |
| 3. Washing with water | " | 2 min |
| 4. Fixing | " | 4 min |
| 5. Washing with water | " | 4 min |
| 6. Stabilizing bath | " | 1 min |

The processing solutions used had the following compositions:

| Color Developer Solution | |
|---|---|
| 4-Amino-N—ethyl-N—(β-methanesulfonamidoethyl)aniline Monosulfate | 5 g |
| Sodium Sulfite | 5 g |
| Hydroxylamine Sulfate | 2 g |
| Potassium Carbonate | 30 g |
| Potassium Hydrogen Carbonate | 1.2 g |
| Potassium Bromide | 1.2 g |
| Sodium Chloride | 0.2 g |
| Trisodium Nitrilotriacetate to adjust pH to 10.1 | 1.2 g |
| Water to make | 1,000 ml |
| Bleaching Solution | |
| Iron (III) Ammonium Ethylenediaminetetraacetate | 100 g |
| Disodium Ethylenediaminetetraacetate | 10 g |
| Potassium Bromide | 150 g |
| Glacial Acetic Acid | 10 g |
| Aqueous Ammonia to adjust pH to 6.0 | |
| Water to make | 1,000 ml |
| Fixing Solution | |
| Ammonium Thiosulfate | 150 g |
| Sodium Sulfite | 10 g |
| Sodium Hydrogen Sulfite to adjust pH to 6.0 | 2.5 g |
| Water to make | 1,000 ml |
| Stabilizing Bath | |
| Formalin (37%) | 5 ml |
| Fuji Drywell | 3 ml |
| Water to make | 1 liter |

Further, each of the samples coated was also stored for 6 months under normal conditions, i.e., at 25° C. and 60% RH, and then exposed and processed in the same manner as described above. The maximum density of magenta color image thus obtained was compared with the maximum density of magenta color image obtained by the development processing just after coating. The results are shown in Table 2 below.

TABLE 2

| Sample | Results of Stability Test<br>Maximum Color Density after Storage/Maximum Color Density just after Coating |
|---|---|
| E | 0.96 |
| F | 0.95 |
| G | 0.95 |
| H | 1.00 |
| U | 0.80 |
| V | 0.79 |
| W | 0.85 |

From the results shown in Table 2, it is apparent that the magenta couplers according to this invention results in only a small decrease in color forming properties when samples containing them are stored after coating, and therefore the stability is excellent, in contrast to the comparative example.

EXAMPLE 3

Samples as described in Example 2 containing the same coupler and additives, except using a silver iodobromide emulsion containing 3 mol% of iodide (containing 100 g of silver halide and 70 g of gelatin per 1 kg of emulsion) in place of the silver halide emulsion used in Example 1, were prepared and subjected to reversal processing as described below. It is apparent from Table 3 below that the stability is improved by using the 2-equivalent magenta couplers according to this invention.

| Processing Step | Temperature (°C.) | Time (minutes) |
|---|---|---|
| 1. First development | 38 | 3 |
| 2. Washing with water | " | 1 |
| 3. Reversal solution | " | 2 |
| 4. Color development | " | 6 |
| 5. Control | " | 2 |
| 6. Bleaching | " | 6 |
| 7. Fixing | " | 4 |
| 8. Washing with water | " | 4 |
| 9. Stabilizing | " | 1 |
| 10. Drying | " | |

The processing solutions used had the following compositions:

| First Development Solution | |
|---|---|
| Water | 800 ml |
| Sodium Tetrapolyphosphate | 2.0 g |
| Sodium Hydrogen Sulfite | 8.0 g |
| Sodium Sulfite | 37.0 g |
| 1-Phenyl-3-pyrazolidone | 0.35 g |
| Hydroquinone | 5.5 g |
| Sodium Carbonate Monohydrate | 28.0 g |
| Potassium Bromide | 1.5 g |
| Potassium Iodide | 13.0 mg |
| Sodium Thiocyanate | 1.4 g |
| Water to make | 1 l |
| Reversal Solution | |
| Water | 800 ml |
| Hexasodium Nitrilo-N,N,N—trimethylene Phosphonic Acid | 3.0 g |
| Stannous Chloride Dihydrate | 1.0 g |
| Sodium Hydroxide | 8.0 g |
| Glacial Acetic Acid | 15.0 ml |
| Water to make | 1 l |
| Color Development Solution | |
| Water | 800 ml |
| Sodium Tetrapolyphosphate | 2.0 g |
| Benzyl Alcohol | 5.0 ml |
| Sodium Sulfite | 7.5 g |
| Trisodium Phosphate (12 hydrate) | 36.0 g |
| Potassium Bromide | 1.0 g |
| Potassium Iodide | 90.0 mg |
| Sodium Hydroxide | 3.0 g |
| Citrazic Acid | 1.5 g |
| 4-Amino-3-methyl-N—ethyl-N—(β-hydroxyethyl)aniline Sesquisulfate Monohydrate | 11.0 g |
| Ethylenediamine | 3.0 g |
| Water to make | 1.0 l |
| Control Solution | |
| Water | 800 ml |
| Glacial Acetic Acid | 5.0 ml |
| Sodium Hydroxide | 3.0 g |
| Dimethylaminoethaneisothiourea Dihydrochloride | 1.0 g |
| Water to make | 1 l |
| Bleaching Solution | |
| Water | 800 ml |

| -continued | |
|---|---|
| Sodium Ethylenediaminetetraacetate Dihydrate | 2.0 g |
| Ammonium Iron (III) Ethylenediamine-tetraacetic Dihydrate | 120.0 g |
| Potassium Bromide | 100.0 g |
| Water to make | 1 l |
| Fixing Solution | |
| Water | 800 ml |
| Ammonium Thiosulfate | 80.0 g |
| Sodium Sulfite | 5.0 g |
| Sodium Hydrogen Sulfite | 5.0 g |
| Water to make | 1 l |
| Stabilizing Bath | |
| Water | 800 ml |
| Formalin (37%) | 5.0 ml |
| Fuji Drywell | 5.0 ml |
| Water to make | 1.0 l |

EXAMPLE 4

A solution, prepared by heating at 60° C. and dissolving a mixture comprising 18 g of Coupler (5) in accordance with this invention, 20 ml of dioctyl butyl phosphate, and 60 ml of ethyl acetate, was added to 250 ml of a 60° C. aqueous solution containing 2.5 g of gelatin and 0.75 g of sodium dodecylbenzenesulfonate. The resulting solution was mechanically vigorously stirred using a homogenizer to obtain a coupler emulsion dispersion. This emulsion dispersion was mixed with 200 g of a photographic emulsion containing $11.2 \times 10^{-2}$ mol of silver chlorobromide (silver bromide: 45 mol%, silver chloride: 55 mol%) and 20 g of gelatin. Then, 10 ml of a 3% aqueous solution of 2-hydroxy-4,6-dichloro-s-triazine sodium salt was added thereto as a hardener and, after adjusting the final pH to 6.5, the solution was coated on a cellulose triacetate film support in a dry thickness of 4.5μ (Film I). This film contained $1.58 \times 10^{-3}$ mol/m² of Coupler (5) and $6.3 \times 10^{-3}$ mol/m² of silver chlorobromide.

Films J, K and P were prepared in the same manner as described for Film I, except for using the equimolar amount (0.028 mol) of each of Couplers (7), (19), and (26) according to this invention in place of the above described Coupler (5).

Further, Films Q, X, and Y were prepared in the same manner as described in Film I, except for using an equimolar amount of each of Couplers (a), (b), and (d), respectively, having the structures shown below as comparison couplers in place of the above described Coupler (5).

Comparison Coupler (a)

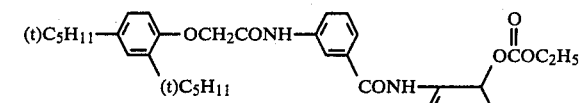

Comparison Coupler (b)

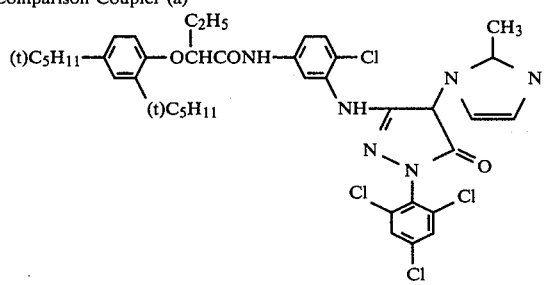

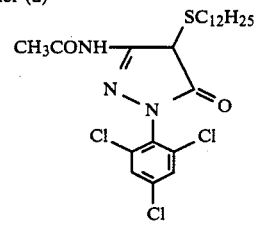

Comparison Coupler (d)

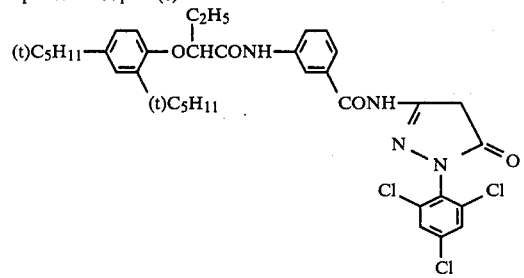

Furthermore, Film Z was prepared in the same manner as described for Film I, except for dispersing the equimolar amount of 4-equivalent Coupler (e) as shown below as a comparison coupler in place of the abovedescribed Coupler (5) and mixing with 400 g of the silver halide emulsion (instead of the 200 g used in Film I).

Comparison Coupler (e)

The dry thickness of the layers and coated amounts of coupler and silver chlorobromide emulsion on the films were shown in Table 3 below.

These films were subjected to stepwise exposure to green light and the following development steps:

| Color Development Processing: | | |
|---|---|---|
| 1. Color development | 38° C. | 3 min 15 sec |
| 2. Bleaching | " | 6 min 30 sec |
| 3. Washing with water | " | 2 min |
| 4. Fixing | " | 4 min |
| 5. Washing | " | 4 min |

The processing solutions used had the following compositions:

| Color Development Solution | |
|---|---|
| 4-Amino-3-methyl-N—ethyl-N—β-hydroxyethylaniline Sesquisulfate | 5 g |
| Sodium Sulfite (anhydrous) | 5 g |
| Hydroxylamine Sulfate | 2 g |
| Potassium Carbonate | 30 g |
| Potassium Hydrogen Carbonate | 1.2 g |
| Potassium Bromide | 1.2 g |
| Sodium Chloride | 0.2 g |
| Trisodium Nitrilotriacetate | 1.2 g |

-continued

| | |
|---|---|
| Water to make | 1 l |
| | (pH = 10.1) |
| Bleaching Solution | |
| Ammonium Salt of Ferric Ethylene-diaminetetraacetate | 100 g |
| Disodium Ethylenediaminetetraacetate | 10 g |
| Potassium Bromide | 150 g |
| Hydroxylamine Acetate | 10 g |
| Water to make | 1 l |
| | (pH = 6.0) |
| Fixing Solution | |
| Ammonium Thiosulfate | 150 g |
| Sodium Sulfite | 10 g |
| Sodium Hydrogen Sulfite | 2.5 g |
| Water to make | 1 l |
| | (pH = 6.0) |

After processing, the optical density of these film samples was measured using green light. As a result, the photographic properties shown in Table 3 were obtained.

TABLE 3

| | | Photographic Properties | | | | | | |
|---|---|---|---|---|---|---|---|---|
| | | Coated Amount (mol/m$^2$) | | Ag/Coupler (molar ratio) | Film Thickness ($\mu$) | Fog | Gamma | Relative Sensitivity | Maximum Color Density |
| Film | Coupler | Coupler | Ag | | | | | | |
| I | (5) | 1.58 × 10$^{-3}$ | 6.3 × 10$^{-3}$ | 4 | 4.5 | 0.02 | 2.10 | 100 | 2.56 |
| J | (7) | 1.56 × 10$^{-3}$ | 6.2 × 10$^{-3}$ | 4 | 4.5 | 0.02 | 2.20 | 95 | 2.42 |
| K | (19) | 1.58 × 10$^{-3}$ | 6.3 × 10$^{-3}$ | 4 | 4.5 | 0.03 | 2.15 | 98 | 2.40 |
| P | (26) | 1.60 × 10$^{-3}$ | 6.4 × 10$^{-3}$ | 4 | 4.5 | 0.02 | 2.18 | 103 | 2.48 |
| Q | (a) | 1.58 × 10$^{-3}$ | 6.3 × 10$^{-3}$ | 4 | 4.5 | 0.03 | 1.92 | 75 | 1.98 |
| X | (b) | 1.61 × 10$^{-3}$ | 6.4 × 10$^{-3}$ | 4 | 4.5 | 0.03 | 1.95 | 69 | 1.83 |
| Y | (d) | 1.57 × 10$^{-3}$ | 6.3 × 10$^{-3}$ | 4 | 4.5 | 0.04 | 1.96 | 81 | 2.00 |
| Z | (e) | 1.56 × 10$^{-3}$ | 12.5 × 10$^{-3}$ | 8 | 5.4 | 0.03 | 1.86 | 62 | 1.75 |

From the comparison of the results of Films I through Z, it is shown that the coupler according to this invention provides higher sensitivity, higher gradation and higher maximum color density than the 4-equivalent couplers even when the ratio of silver halide/coupler was reduced to about ½.

Also, the couplers according to this invention have superior color forming properties compared to previously known couplers, as is apparent from the comparison of the results obtained using Couplers (a), (b) and (d).

EXAMPLE 5

The following processings were conducted after exposure of additional Films I, J, K, Q, and Z as described in Example 4.

| Color Development Processing | | |
|---|---|---|
| 1. Color Development | 30° C. | 4 min |
| 2. Bleach-Fixing | " | 2 min |
| 3. Washing | " | 2 min |
| 4. Stabilizing Bath | " | 2 min |

The photographic properties of the thus obtained films are shown in Table 4 below.

Furthermore, as aqueous stabilizing baths a formaldehyde free Stabilizing Bath (a) and Stabilizing Bath (b) containing 1% of a 40% by weight aqueous solution of formaldehyde were used. With the two films having been processed, the reduction ratio of the density based on the initial density, after leaving the films at 80° C. for 2 weeks, was determined, and the results are tabulated in Table 5 below.

| | |
|---|---|
| Color Developer | |
| Sodium Metaborate | 25 g |
| Sodium Sulfite | 2 g |
| Hydroxylamine (sulfate) | 2 g |
| Potassium Bromide | 0.5 g |
| 6-Nitrobenzimidazole (nitrate) | 0.02 g |
| Sodium Hydroxide | 4 g |
| Diethylene Glycol | 20 ml |
| 4-N—Ethyl-N—β-methanesulfonamido-ethyl)amino-2-methylaniline Sesquisulfate | 8 g |
| Water to make | 1 l |
| | pH = 10.2 |
| Bleach-Fixing Solution | |
| Ferric Salt of Ethylenediaminetetraacetic Acid | 45 g |
| Ammonium Thiocyanate | 10 g |
| Sodium Sulfite | 10 g |
| Ammonium Thiosulfate (60% aq. soln.) | 100 ml |
| Sodium Ethylenediaminetetraacetate | 5 g |
| Water to make | 1 l |
| | pH = 6.9 |
| Stabilizing Bath (a) | |
| Tartaric Acid | 10 g |
| Zinc Sulfate | 10 g |
| Sodium Metaborate | 20 g |
| Water to make | 1 l; or |
| Stabilizing Bath (b) | |
| Tartaric Acid | 10 g |
| Zinc Sulfate | 10 g |
| Sodium Metaborate | 20 g |
| Formalin (40%) | 10 ml |
| Water to make | 1 l |

TABLE 4

| | | Photographic Properties (using Stabilizing Bath (a)) | | |
|---|---|---|---|---|
| Film | Coupler | Fog | Gamma | Maximum Color Density |
| I | (5) | 0.03 | 2.16 | 2.63 |
| J | (7) | 0.03 | 2.28 | 2.58 |
| K | (19) | 0.03 | 2.17 | 2.55 |
| Q | (a) | 0.03 | 1.90 | 1.98 |
| Z | (e) | 0.03 | 1.75 | 1.72 |

TABLE 5

| | | Fastness of Color Image (after storage for 2 weeks at 80° C.) | | |
|---|---|---|---|---|
| | | Reduction Ratio (%) in Color Image Density | | |
| | Stabilizing | Initial Density | | |
| Film | Bath | 0.5 | 1.0 | 2.0 |
| I | (a) | 6 | 4 | 3 |
| | (b) | 6 | 3 | 3 |
| J | (a) | 5 | 3 | 3 |

TABLE 5-continued

| | | Fastness of Color Image (after storage for 2 weeks at 80° C.) | | |
|---|---|---|---|---|
| | | Reduction Ratio (%) in Color Image Density | | |
| | Stabilizing | Initial Density | | |
| Film | Bath | 0.5 | 1.0 | 2.0 |
| K | (b) | 5 | 3 | 3 |
| | (a) | 5 | 4 | 4 |
| | (b) | 4 | 3 | 3 |
| Z | (a) | 70 | 43 | 14 |
| | (b) | 9 | 8 | 6 |

The results in Table 4 show that excellent color forming properties can be obtained with the couplers according to this invention even when processing at a low temperature and for a short time. This fact indicates that the couplers according to this invention have a high developing activity and a high conversion rate of a coupler to dye.

The results in Table 5 show that Films I, J, and K provide sufficient heat fastness even without stabilization using formaldehyde in a conventional manner.

While the invention has been described in detail and with reference to specific embodiments thereof, it will be apparent to one skilled in the art that various changes and modifications can be made therein without departing from the spirit and scope thereof.

What is claimed is:

1. A color photographic light-sensitive material comprising a support having coated thereon at least one silver halide emulsion layer containing a 5-pyrazolone magenta coupler represented by formula (I)

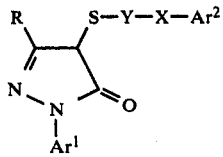

wherein R represents an acylamino group, an anilino group or a ureido group; $Ar^1$ represents a phenyl group which may be substituted with one or more halogen groups, alkyl groups, or alkoxy groups; $Ar^2$ represents a phenyl group or a naphthyl group, each of which may be substituted with one or more halogen groups, hydroxy groups, carboxy groups, cyano groups, alkyl groups, acylamino groups, carbamoyl groups, ureido groups, sulfonamido groups, diacylamino groups, sulfamoyl groups, alkoxycarbonyl groups, phenyl groups, arylsulfonyl groups or alkoxy groups; X represents oxygen; and Y represents a straight chain or branched chain alkylene group having from 1 to 6 carbon atoms, or an alkylene group containing an ether bond.

2. A color photographic light-sensitive material as in claim 1, wherein said 5-pyrazolone magenta coupler is diffusion resistant.

3. A color photographic light-sensitive material as in claim 1 or 2, wherein said silver halide emulsion layer is a green-sensitive silver halide emulsion layer.

4. A color photographic light-sensitive material as in claim 3, wherein said photographic material further contains at least one blue-sensitive silver halide emulsion layer containing a yellow color forming coupler and at least one red-sensitive silver halide emulsion layer containing a cyan color forming coupler.

5. A color photographic light-sensitive material as in claim 1 or 2, wherein said 5-pyrazolone magenta coupler is present at a coverage of from about $1 \times 10^{-4}$ to $5 \times 10^{-3}$ mol/m$^2$.

6. A color photographic light-sensitive material as in claim 4, wherein said 5-pyrazolone magenta coupler is present at a coverage of from about $1 \times 10^{-4}$ to $5 \times 10^{-3}$ mol/m$^2$.

7. A color photographic light-sensitive material as in claim 1 or 2, wherein said 5-pyrazolone magenta coupler is present at a coverage of from about $3 \times 10^{-4}$ to $2 \times 10^{-3}$ mol/m$^2$.

8. A color photographic light-sensitive material as in claim 4, wherein said 5-pyrazolone magenta coupler is present at a coverage of from about $3 \times 10^{-4}$ to $2 \times 10^{-3}$ mol/m$^2$.